(12) United States Patent
Bezrucka et al.

(10) Patent No.: US 11,648,151 B2
(45) Date of Patent: May 16, 2023

(54) WELDING HELMET

(71) Applicant: Fronius International GmbH, Pettenbach (AT)

(72) Inventors: Patrick Bezrucka, Pettenbach (AT); Helmut Friedl, Pettenbach (AT)

(73) Assignee: Fronias International GmbH, Pettenbach (AT)

( * ) Notice: Subject to any disclaimer, the term of this patent is extended or adjusted under 35 U.S.C. 154(b) by 0 days.

(21) Appl. No.: 17/638,271

(22) PCT Filed: Jan. 29, 2021

(86) PCT No.: PCT/EP2021/052063
§ 371 (c)(1),
(2) Date: Feb. 25, 2022

(87) PCT Pub. No.: WO2021/152063
PCT Pub. Date: Aug. 5, 2021

(65) Prior Publication Data
US 2022/0296419 A1    Sep. 22, 2022

(30) Foreign Application Priority Data
Jan. 31, 2020   (EP) .................................. 20154862

(51) Int. Cl.
*A61F 9/06*  (2006.01)
*A42B 3/22*  (2006.01)

(52) U.S. Cl.
CPC .............. *A61F 9/067* (2013.01); *A42B 3/225* (2013.01)

(58) Field of Classification Search
CPC ................................ A61F 9/067; A42B 3/225
See application file for complete search history.

(56) References Cited

U.S. PATENT DOCUMENTS

| 6,891,681 B2 | 5/2005 | Schindele |
| 11,061,262 B2 * | 7/2021 | Esposito ................. A61F 9/067 |
| 2005/0017152 A1 | 1/2005 | Fergason |

(Continued)

FOREIGN PATENT DOCUMENTS

| CN | 109276368 A | 1/2016 |
| DE | 20 2011 105 435 U1 | 10/2011 |

(Continued)

OTHER PUBLICATIONS

International Search Report of PCT/EP2021/052063, dated May 10, 2021.

(Continued)

*Primary Examiner* — Dung T Nguyen
(74) *Attorney, Agent, or Firm* — Collard & Roe, P.C.

(57) ABSTRACT

A welding helmet includes at least one helmet shell, fixing elements, a glare shield device and at least one protective screen spaced therefrom, and at least one display device for presenting data in the field of view of a welder, the at least one display device being arranged in the edge region of the field of view in the intermediate space between the glare shield device and the protective screen. The glare shield device has at least one cut-out in the area of the at least one display device. Because there is no glare shield device in the region of the display device, the view of the display device is not impeded by the glare shield device.

15 Claims, 5 Drawing Sheets

(56) References Cited

U.S. PATENT DOCUMENTS

2010/0088793 A1    4/2010   Ghisleni et al.
2016/0163221 A1*   6/2016   Sommers ................. A61F 9/06
                                                                                                                434/234

FOREIGN PATENT DOCUMENTS

| EP | 3 192 481 A1 | 7/2017 |
| EP | 3192481 A1 | 7/2017 |
| EP | 3 326 592 A1 | 5/2018 |
| EP | 2 488 135 B1 | 9/2018 |
| JP | 2006-239392 A | 9/2006 |
| WO | 96/36303 A1 | 11/1996 |
| WO | 01/81819 A1 | 11/2001 |
| WO | 2007/140642 A1 | 12/2007 |

OTHER PUBLICATIONS

European Search Report dated Jul. 31, 2020 in European Application No. 20154862.5 with English translation of relevant parts.
Chinese Office Action in Chinese Application No. 202180005056.4 dated Oct. 26, 2022.
Japanese Office Action in Japanese Patent Application No. 2022-546062 dated Feb. 14, 2023 with English translation.

* cited by examiner

WELDING HELMET

CROSS REFERENCE TO RELATED APPLICATIONS

This application is the National Stage of PCT/EP2021/052063 filed on Jan. 29, 2021, which claims priority under 35 U.S.C. § 119 of European Application No. 20154862.5 filed on Jan. 31, 2020, the disclosure of which is incorporated by reference. The international application under PCT article 21(2) was not published in English.

The invention relates to a welding helmet having at least one helmet shell, fixing elements, a glare shield device and at least one protective screen spaced therefrom, and at least one display device for presenting data in the field of view of a welder, the at least one display device being arranged in the edge region of the field of view in the intermediate space between the glare shield device and the protective screen.

For a long time now it has been customary to protect the eyes of the welder against the bright light of the arc that occurs during welding. The original visor is increasingly being replaced by welding helmets with a glare shield device, which in addition to the protection function for the eyes also provides a mechanical protection function for the welder's head as well as protection against the inhalation of toxic fumes that can occur during welding. The glare shield device may have various designs, for example in the form of a device protecting both eyes of the welder or two separate devices, one for each eye of the welder. Whereas in the past simple darkened films were used, nowadays automatic darkening devices in the form of so-called auto-darkening filter cartridges are used.

In addition to darkening the glare shield device, e.g. after the ignition of the arc or by an appropriate remote control, it is increasingly common to display various data or similar in the field of view of the welder who is wearing the welding helmet. This means that when carrying out the welding process, the welder does not have to turn their eyes away from the welding site in order to read data (e.g. welding parameters) or similar from a display of the welding unit, or similar. The term protective screen usually refers to attachment panels which are arranged in front of the glare shield device. However, in some designs of welding helmets, the glare shield device can also be removed or flipped up in the manner of a visor, and a protective screen arranged behind it in the welding helmet protects the welder's eyes. The protective screen can also be designed as an optical glass.

The fact that the at least one display device is arranged in a particularly simple manner in an available intermediate space between the glare shield device of the welding helmet and the protective screen enables the display device to be optimally protected against dust, sweat, fumes and other contaminants as well as mechanical stresses and other environmental influences. Due to the protected arrangement of the at least one display device in the intermediate space, the welding helmet can be used for a particularly long time without needing maintenance of the display device.

For example, EP 3 326 592 A1, EP 3 192 481 A1, and WO 2007/140642 A1 describe welding helmets or welding masks with a glare shield device as well as a "head-up display" for displaying welding parameters or similar of the type relevant to the invention.

EP 2 488 135 B1 describes a welding helmet with an integrated user interface, wherein the presentation of data or the like is effected in such a way that it is displayed in the same focus plane as the welding process itself. This means that the welder does not have to turn away from the welding process in order to be able to read the desired data or similar.

Finally, US 2016/0163221 A1 describes a welding helmet with data glasses arranged underneath, onto which welding parameters can be displayed in the welder's field of view so that the welder can read the data even without turning their gaze away from the welding site.

Apart from the fact that in many cases the displayed data limit the field of view of the welder too greatly and prevent an unobstructed view of the weld seam, the display devices of known welding helmets are often unprotected or inadequately protected, so that they are exposed to dust, welding fumes and other contaminants as well as mechanical stresses. A further disadvantage is that previous displays in welding helmets or data glasses do not take into account any visual defects of the welder.

The object of the present invention consists in the creation of a welding helmet mentioned above with at least one display device for presenting data, which display device is protected from the usual environmental influences occurring during welding, so that the longest possible service life is guaranteed. The field of view of the welder should be limited as little as possible by the presented data, in order to ensure the clearest possible view of the weld seam. The welding helmet should also be designed as simply and cost-effectively as possible to ensure a wide range of applications. Disadvantages of known welding helmets are to be avoided or at least reduced.

The object according to the invention is achieved by the fact that the glare shield device in the area of the at least one display device has at least one cut-out. According to the invention, no glare shield device is arranged in the areas of the display device, which means that the view to the display device is not restricted by the glare shield device. At positions where a display device is arranged, the potentially complex and expensive glare shield device can be dispensed with. Alternatively, the glare shield device may also be arranged at the points of the display device at which no darkening is performed during the welding process, however, so that the view of the display device is not impaired. To avoid a feeling of dizziness ("motion sickness") on the part of the welder, for example, the data is only displayed when required or when requested and not permanently. If two display devices are placed in the welding helmet on the right and left of the welder's field of view, different data can be displayed for the left and right eye of the welder or a three-dimensional effect can be created by displaying the same information. The fact that the at least one display device is arranged in the welding helmet in the edge region of the welder's field of view means that the view of the work area is restricted to a very minor extent, wherein the welder can quickly read the data displayed on the display device by means of appropriate eye movements without turning their gaze away from the welding. Modern technology allows a miniaturized implementation of the at least one display device, which makes an arrangement possible even with small intermediate gaps between the glare shield device and the protective screen. In addition, such display devices are available at very low cost, which also makes it possible to retrofit a welding helmet with at least one such device. It is also possible to convert the welding helmet to different display devices quickly and easily. By displaying the data about the welding process while the welding process is carried out, the welder does not need to turn their eyes away from the work area, which enables optimum welding quality to be achieved.

If the at least one display device is arranged adjustably in the intermediate space, the position of the display device in relation to the eye or eyes of the welder can be adjusted quickly and easily. The adjustability of the display device can be achieved by various mechanical structures, such as adjusting screws or similar, but also by electrical structures, such as stepper motors or similar. If two display devices are arranged in the welding helmet, the adjustability also allows the device to be adjusted to the position of the welder's eyes relative to each other.

It is particularly advantageous if the at least one display device is adjustable via at least one drive. By means of at least one such preferably electric drive, the adjustment of the at least one display device can also be performed while wearing the welding helmet until the welder obtains an optimal result. The adjustment of the at least one drive can also be performed in a particularly convenient way using tools such as smartphones, notebooks or similar, via suitable apps or software programs. The settings can preferably also be stored so that they can be retrieved when necessary and adapted to the particular welder wearing the welding helmet.

A seal, preferably made of elastic material, may be arranged between the glare shield device and the at least one display device. Such a seal, which is preferably elastic, will better protect the at least one display device from vibration and also prevent dirt from entering the inside of the display device. Such a seal, which is preferably not permanently connected to the glare shield device, also facilitates replacement of the display device since after removal of the protective screen the display device is simply replaced and the seal is placed between the display device and the glare shield device. The seal can also be rigidly connected to the housing of the display device, which means that the display device is automatically sealed against the glare shield device when positioned in the intermediate space between the glare shield device and the protective screen.

Advantageously, the at least one display device is connected to an existing control device. The connection between the display device and the control device of the welding helmet can be effected by cables, preferably via suitable plug connections, or also wirelessly. Both data and the supply voltage to the respective components are transmitted via the connection. This makes it possible to retrofit the welding helmet with at least one display device or to replace it in a simple manner. The control device can be both integrated or arranged in the welding helmet itself, or else in a unit that is positioned apart from it. The display device can be optimally controlled via the control device of the welding helmet and thus can be used to define which data is displayed on the display device and made available to the welder as necessary. The control device is usually formed by a microprocessor which is programmed accordingly to fulfil the corresponding controls of the glare shield device and the at least one display device of the welding helmet.

If the at least one display device is connected to the protective screen, the display device can be replaced easily and quickly by removing and subsequently refitting the protective screen. The connection between display device and protective screen can be made, for example, by bonding, screws, or the like.

The at least one display device preferably contains a display, in particular a colour display, and at least one optical device. Such display devices are available in small sizes and at particularly low prices. The display device is usually connected to a corresponding control device and the required power supply via a corresponding cable connection. Ideally, a power supply can also be contained in the display device in the form of a small battery or an accumulator and the connection to a control device can also be implemented wirelessly. The optical device can be formed by a lens, a mirror, or an optical fibre, or even combinations thereof, which directs the image to be displayed to the desired location.

At least one correction optics may be located between the at least one display device and the glare shield device in order to compensate for visual defects and positioning errors of the welder's eyes. For individual adaptation to the respective welder, it is advantageous if the at least one additional correction optics is easily replaceable.

If the at least one display device is connected to at least one sensor, additional functions can be achieved. By connecting the respective sensor to a control device in the welding helmet, various assistive functions can be achieved.

At least one sensor can be arranged on the side of the display device facing the protective screen. Such a sensor can be used to control the display device or other functions of the welding helmet, the welding system or welding equipment. For example, a mechanical sensor can be used to switch between functions of the welding helmet or welding system by manual actuation in the area of the protective screen. Using appropriate optical (e.g. infrared sensors), capacitive, inductive or other sensors, the control can also be carried out in a contactless manner by the welder placing a hand in front of the sensor, causing a changeover. However, other sensors, such as light sensors, can also be used to control the display brightness of the display device.

At least one sensor can be formed by a camera, a microphone, a light sensor, a touch sensor, and/or a temperature sensor. When using a camera as a sensor, gesture control by the welder's hand can be used to makes changes to the display device or other functions of the welding helmet or welding system. For example, at least one microphone can be used to record the ambient noise or the sounds generated by the arc during welding, or to control certain functions. It is also conceivable, for example, to control the display device or other functions of the welding helmet or the welding system via speech. Motion sensors as well as position sensors or gyroscope sensors can be used to provide control as a function of the position or orientation of the welding helmet.

If a nose opening is provided on the welding helmet, and the at least one display device is arranged next to the nose opening, this results in an optimal and space-saving arrangement of the at least one display device without restricting the view of the work area. Depending on the design of the welding helmet, the arrangement of the at least one display device above the nose opening may also be appropriate.

According to another feature of the invention, the glare shield device is formed by an auto-darkening filter cartridge. Such an auto-darkening filter cartridge is usually formed by a liquid crystal display and can be switched particularly quickly between different degrees of darkening. This means, for example, in a short-circuit based welding process, the display can be brightened during the short-circuits when no arc is burning, thereby improving the view of the weld seam. At positions of the auto-darkening filter cartridge where more protection is required, the darkening can also be set to a higher level locally or at specific points.

If the at least one display device is connected to a transceiver, the data can be transmitted to a control panel or to an appropriate control device. The control device may be arranged on or inside the welding helmet or remotely from it. The transceiver can operate both by wired and wireless means.

The present invention will be explained in further detail by reference to the attached drawings. Shown are.

Figure 1:
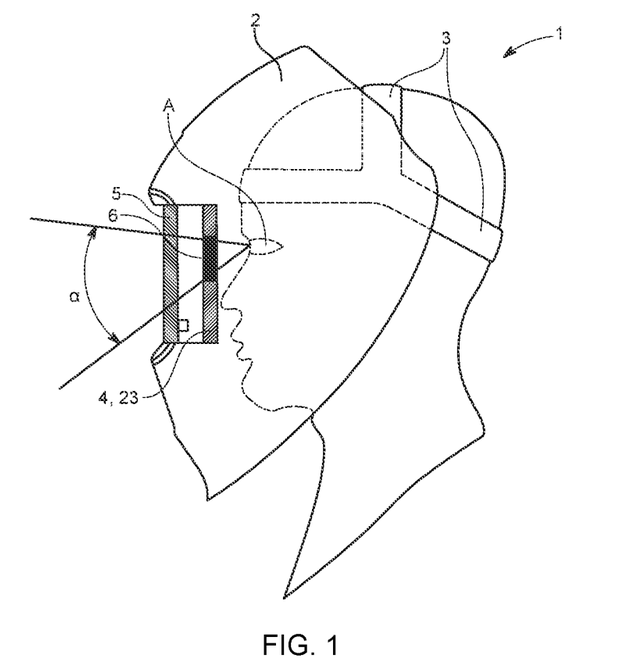
FIG. 1 a standard welding helmet in a lateral, partially cut view, with at least one helmet shell, fastening elements, a glare shield device, at least one protective screen, and at least one display device for displaying data in the field of view of a welder.

FIG. 1 shows a standard welding helmet 1 in a lateral, partially cut view, with at least one helmet shell 2, appropriate fastening elements 3, such as belts or straps, a glare shield device 4, at least one protective screen 5, and at least one display device 6 for presenting data in the field of view of a welder. In the illustration, a protective screen 5 in the form of an attachment panel is arranged in front of the glare shield device 4. Welding helmets 1 are also known where the glare shield device 4 together with the protective screen 5 in the form of an attachment panel can be flipped up in the manner of a visor and where a further protective screen 5 for protecting the welder's eyes when the visor is flipped up is arranged behind it (not shown). The data to be displayed on the display device 6 are usually welding parameters such as current strength, wire feed, voltage, welding job, but also error messages, positive feedback messages (e.g. weld seam OK), and warnings that are of interest to the welder. In the case of standard welding helmets 1, the at least one display device 6 is located in the field of view of the welder wearing the welding helmet 1 and is formed, for example, by a corresponding "head-up display". The viewing angle of the eye A of the welder is also indicated by α. Because the relevant data is displayed in the field of view of the welder, the welder does not need to turn their gaze away from the weld seam or the work area during the welding process. On the other hand, such display devices 6 are relatively expensive and complex and in some circumstances the display of the relevant data may restrict the view of the weld point or the weld seam. The glare shield device 4 is preferably formed by an auto-darkening filter cartridge 23. In order to prevent the welder from suffering from dizziness, it is advantageous that the at least one display device 6 is activated only when required or when requested, and not permanently. This also means that the view of the work area is not unnecessarily impaired.

Figure 2:
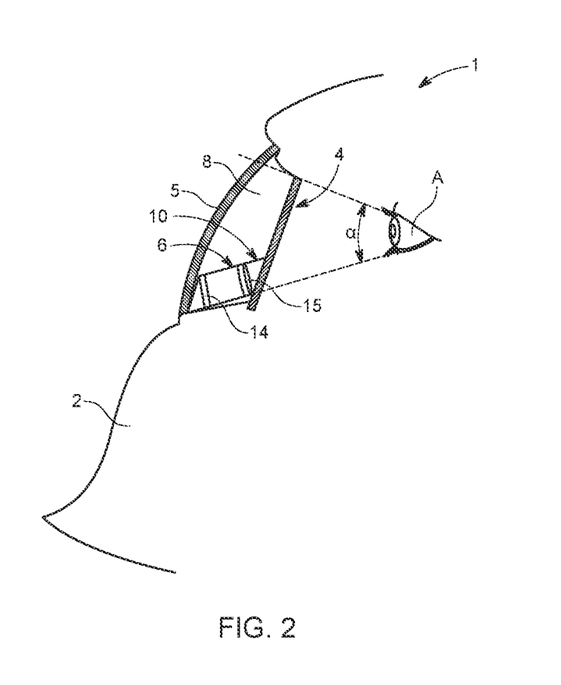
FIG. 2 a lateral, partially cut view of a welding helmet with a display device arranged in the intermediate space between the glare shield device and the protective screen at the lower edge of the field of view.

FIG. 2 shows a lateral, partially cut view of a welding helmet 1 with a display device 6 arranged in the intermediate space 8 between the glare shield device 4 and the protective screen 5 at the lower edge of the welder's field of view. Because the at least one display device 6 is arranged in the intermediate space 8 between the glare shield device 4 and the protective screen 5, the device is protected from dirt, dust, etc. and can therefore be used for a long time without maintenance. In addition, the at least one display device 6 is optimally protected against mechanical stress. The arrangement of the at least one display device 6 at the edge of the welder's field of view ensures that the viewing angle α of the welder is disturbed as little as possible, but nevertheless enables the relevant data to be easily read from the display device 6. A seal 10 is preferably arranged between the display device 6 and the glare shield device 4. This seal 10 is preferably made of elastic material, in particular a plastic material. The seal 10 provides better protection for the display device 6 against mechanical shocks and additionally prevents any contamination of the display device 6. The display device 6 is connected to a control device of the welding helmet 1 via appropriate cables and plug connections (see FIG. 10). The display device 6 can be connected to the protective screen 5 in order to be able to replace it as simply and quickly as possible. The display device 6 consists at least of a display 14 and a corresponding optical device 15, the display 14 preferably being formed by a colour display. The optical device 15 can be formed by a lens, a mirror, or an optical fibre or combinations thereof.

Figure 3:
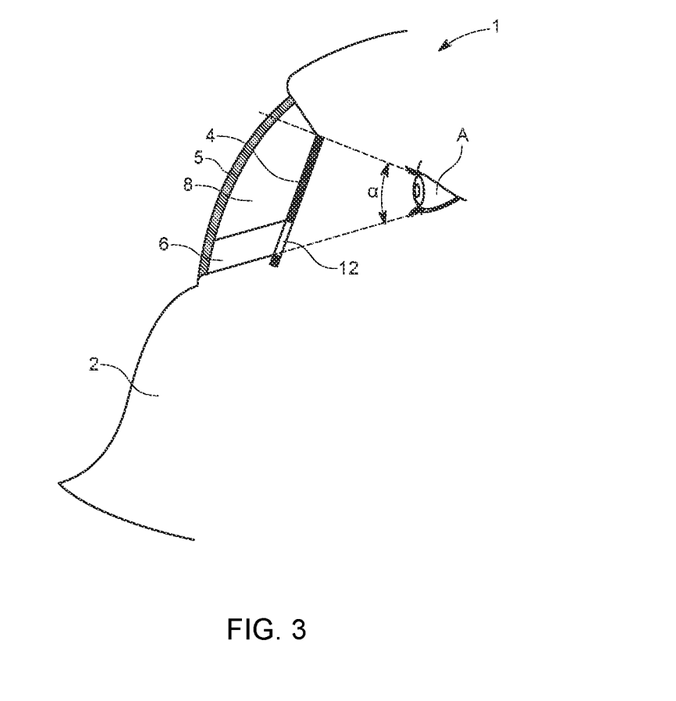
FIG. 3 a lateral, partially cut view of an embodiment according to the invention of a welding helmet with a display device arranged in the intermediate space between the glare shield device and the protective screen at the lower edge of the field of view.

FIG. 3 shows a lateral, partially cut view of an embodiment according to the invention of a welding helmet 1 with a display device 6 arranged in the intermediate space 8 between the glare shield device 4 and the protective screen 5 at the lower edge of the field of view, wherein in this case the glare shield device 4 in the area of the display device 6 has been removed or has a corresponding opening 12 or a hole. This ensures an unobstructed view of the display device 6 for the welder even with an otherwise darkened glare shield device 4, or alternatively the glare protection device 4, which can be expensive, can be omitted in the area of the display device 6 to save costs.

Figure 4:
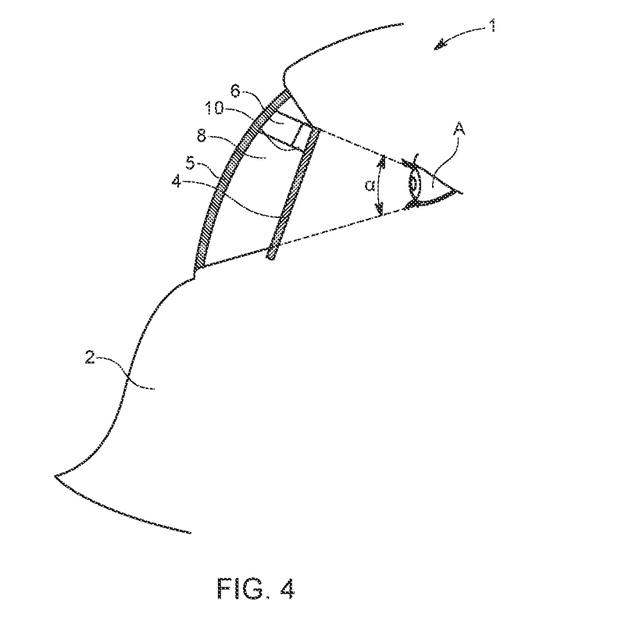
FIG. 4 an alternative embodiment of a welding helmet with a display device arranged in the intermediate space between the glare shield device and the protective screen at the upper edge of the field of view.

FIG. 4 shows an alternative embodiment of a welding helmet 1 with a display device 6 arranged in the intermediate space 8 between the glare shield device 4 and the protective screen 5 at the upper edge of the field of view. Depending on the application, it may be advantageous if the at least one display device 6 is located at the top edge of the viewing angle α of the welder. In the case of welding helmets 1 with a nose opening 22, however, the region next to the nose opening 22 is particularly suitable for arranging one or two display devices 6 (see FIG. 8). The arrangement of two display devices 6 allows different data to be displayed for the left and right eye A of the welder, or a three-dimensional effect to be achieved by arranging the same graphical information for both eyes.

Figure 5:
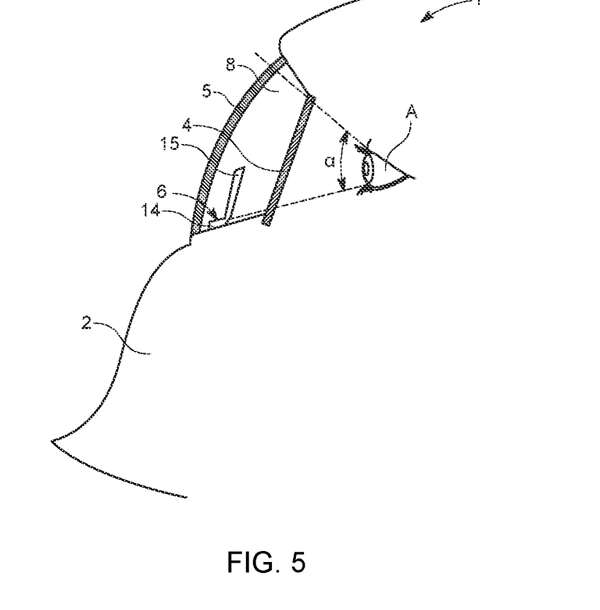
FIG. 5 a further alternative embodiment of a welding helmet with a display device arranged in the intermediate space between the glare shield device and the protective screen.

FIG. 5 shows a further alternative embodiment of a welding helmet 1 with a display device 6 arranged in the intermediate space 8 between the glare shield device 4 and the protective screen 5. The display device 6 has a display 14 and an optical device 15 in the form of an optical fibre pointing upwards in the intermediate space. The optical fibre 15 transfers the image of the display 14 in the manner of a head-up display.

Figure 6:
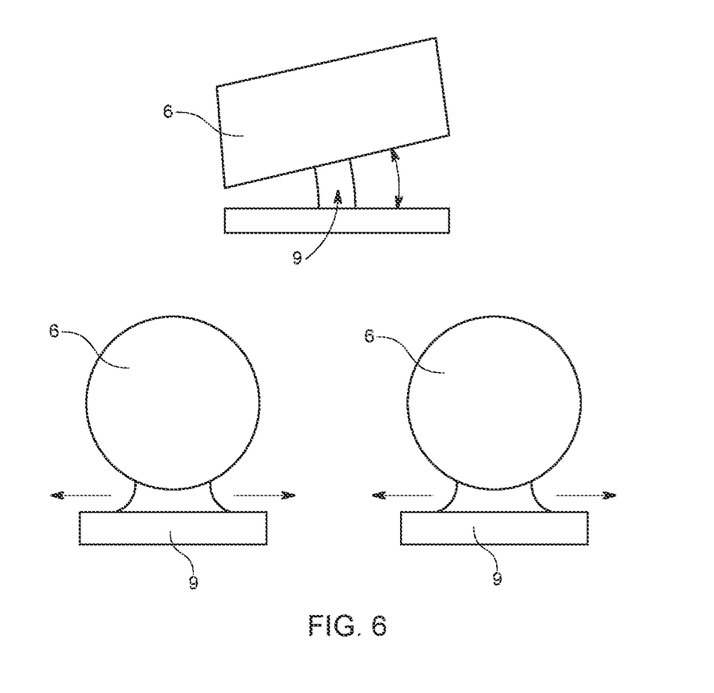
FIG. 6 a detailed view of various embodiments of adjustably mounted display devices.

FIG. 6 shows a detailed view of various embodiments of adjustably mounted display devices 6. To adapt the at least one display device 6 to the position of the eye type of the welder, appropriate means for the adjustable arrangement of the at least one display device 6 are preferably provided. These means of adjustment can be formed by simple mechanical or more complex electromechanical structures. For example, a lateral or vertical displacement of the at least one display device 6 can be achieved by means of corresponding adjusting screws (not shown). But suitable drives 9 can also be used to achieve a tilting or displacement of the at least one display device 6. By displacing the at least one display device 6 laterally, it can be optimally adjusted to the distance between the welder's eyes and an optimal view of the display device 6 can be ensured. As shown, a separate display device 6 may be provided for each eye.

Figure 7:
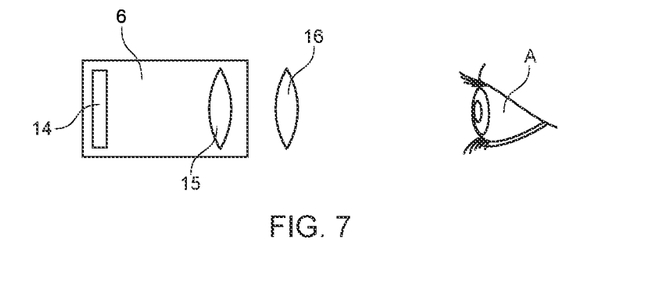
FIG. 7 a detailed view of another embodiment of a display device with correction optics.

FIG. 7 shows a detailed view of another embodiment of a display device 6. In this case, at least one additional correction optics 16 is arranged in front of the display device 6 consisting of a display 14 and an optical device 15, in order to be able to correct any visual defects or visual impairments of the eye A of the welder. The correction optics 16 can also be integrated in the display device 6 or placed directly in front of it, but should be replaceable as easily and quickly as possible in order to ensure an individual adaptation to the welder.

Figure 8:
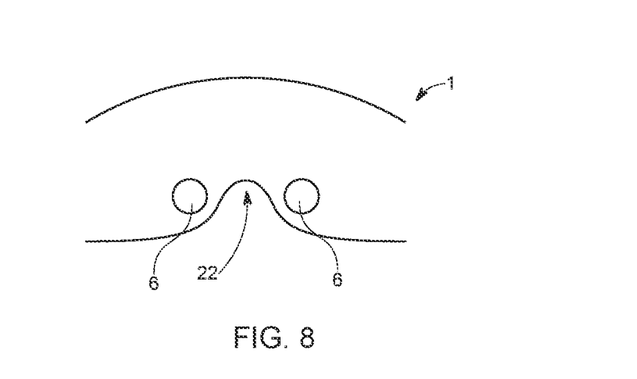
FIG. 8 a schematic view of two display devices arranged next to a nose opening on the welding helmet.

FIG. 8 shows a schematic view of two display devices 6 arranged next to a nose opening 22 on the welding helmet 1. Due to such an arrangement, the field of view of the welder is only minimally disturbed by the display devices 6 while an optimal reading of the data from the display devices 6 is still ensured. In addition, a welding helmet 1 with such a nose opening 22 can be retrofitted particularly simply and cost-effectively with display devices 6.

Figure 9:
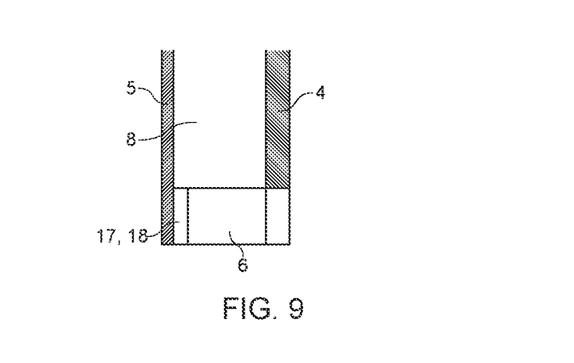
FIG. 9 a section through a detail of a display device with a camera for detecting gestures of the welder.

FIG. 9 shows a section through a detail of a display device 6, arranged in the intermediate space 8 between the glare shield device 4 and the protective screen 5, having a camera 18 as a sensor 17 for detecting gestures made by the welder. Using a sensor 17 on the side of the display device 6 facing the protective screen 5, the display device 6 or other functions of the welding device or welding system can be controlled via the sensor 17. When using a camera 18, for example, gestures made with the welder's hand can be used to trigger specific functions or to activate or switch over the display device 6. Such a sensor 17 or camera 18 can be designed to be particularly small in size and also cost-effective. A camera 18 also allows the weld seam to be imaged and used for later documentation purposes or for quality assurance purposes.

Figure 10:
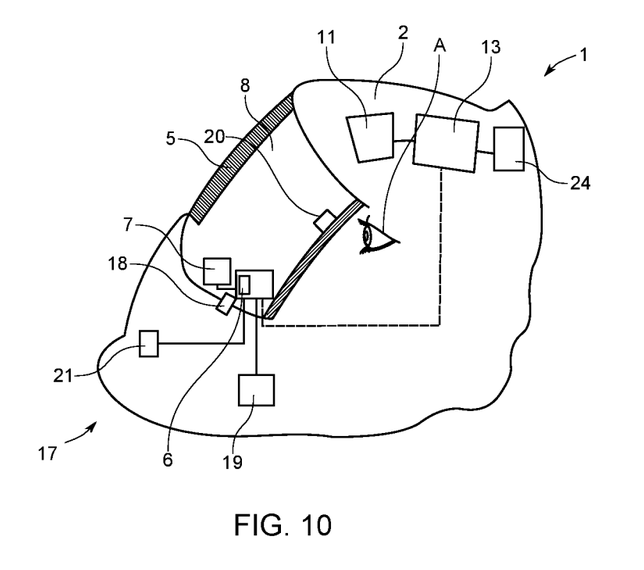
FIG. 10 a schematic representation of a display device for a welding helmet connected to the control device and to various sensors.

Finally, FIG. 10 shows a schematic representation of a display device 6 for a welding helmet 1, connected to the control device 13 and various sensors 17. The at least one display device 6 is connected via appropriate cables or also wirelessly to the control device 13, which is preferably arranged in the welding helmet 1 in any case. By suitable programming of the control device 13, which is usually formed by a microcontroller or similar, the display of the corresponding data in the at least one display device 6 can be controlled. Various additional functions can be achieved by connecting the display device 6 or the control device 13 to corresponding sensors 17. Sensors 17 can be formed by a camera 18, a microphone 19, a light sensor 20 or also a temperature sensor 7. The power supply for the at least one display device 6, as well as the control unit 13 and any sensors 17 present, is provided by means of an energy supply 11 preferably arranged in the welding helmet 1. An accumulator of a fan commonly arranged in welding helmets 1 can also be used for the energy supply (not shown). If the display device 6 or the control device 13 is connected to a transceiver 24, data or information can be transmitted to and received from a higher-level unit, such as the welding unit. The transceiver 24 can be designed to operate by wires or wirelessly.

The invention claimed is:

1. A welding helmet (1) having at least one helmet shell (2), fixing elements (3), a glare shield device (4) and at least one protective screen (5) spaced therefrom, and at least one display device (6) for presenting data in the field of view of a welder, the at least one display device (6) being arranged in the edge region of the field of view in the intermediate space (8) between the glare shield device (4) and the protective screen (5), wherein the glare shield device (4) has at least one cut-out (12) in the area of the at least one display device (6).

2. The welding helmet (1) according to claim 1, wherein the at least one display device (6) is arranged so as to be adjustable in the intermediate space (8).

3. The welding helmet (1) according to claim 2, wherein the at least one display device (6) is adjustable by means of at least one drive (9).

4. The welding helmet (1) according to claim 1, wherein a seal (10) is arranged between the glare shield device (4) and at least one display device (6).

5. The welding helmet (1) according to claim 4, wherein the seal (10) is made of elastic material.

6. The welding helmet (1) according to claim 1, wherein the at least one display device (6) is connected to an available control unit (13).

7. The welding helmet (1) according to claim 1, wherein the at least one display device (6) is connected to the protective screen (5).

8. The welding helmet (1) according to claim 1, wherein the at least one display device (6) contains a display (14) and at least one optical device (15).

9. The welding helmet (1) according to claim 1, wherein at least one correction optics (16) is arranged between the at least one display device (6) and the glare shield device (4).

10. The welding helmet (1) according to claim 1, wherein the at least one display device (6) is connected to at least one sensor (17).

11. The welding helmet (1) according to claim 10, wherein at least one sensor (17) is arranged on the side of the display device (6) facing the protective screen (5).

12. The welding helmet (1) according to claim 11, wherein at least one sensor (17) is formed by a camera (18), a microphone (19), a light sensor (20), a touch sensor (21) and/or a temperature sensor (7).

13. The welding helmet (1) according to claim 1, wherein a nose opening (22) is provided, and wherein the at least one display device (6) is arranged next to the nose opening (22).

14. The welding helmet (1) according to claim 1, wherein the anti-glare device (4) is formed by an auto-darkening filter cartridge (23).

15. The welding helmet (1) according to claim 1, wherein the at least one display device (6) is connected to a transceiver (24).

* * * * *

UNITED STATES PATENT AND TRADEMARK OFFICE
CERTIFICATE OF CORRECTION

| | | |
|---|---|---|
| PATENT NO. | : 11,648,151 B2 | Page 1 of 1 |
| APPLICATION NO. | : 17/638271 | |
| DATED | : May 16, 2023 | |
| INVENTOR(S) | : Patrick Bezrucka et al. | |

It is certified that error appears in the above-identified patent and that said Letters Patent is hereby corrected as shown below:

On the Title Page

On Item (73), please amend the Assignee to correctly read -- Fronius International GmbH --.

Signed and Sealed this
Twenty-sixth Day of December, 2023

Katherine Kelly Vidal
*Director of the United States Patent and Trademark Office*